(12) United States Patent
Papathanassiu

(10) Patent No.: US 7,381,799 B2
(45) Date of Patent: Jun. 3, 2008

(54) COMPOSITIONS AND METHODS FOR INHIBITING ANGIOGENESIS

(75) Inventor: Adonia E. Papathanassiu, Silver Spring, MD (US)

(73) Assignee: Ergon Pharmaceuticals LLC, Washington, DC (US)

( * ) Notice: Subject to any disclaimer, the term of this patent is extended or adjusted under 35 U.S.C. 154(b) by 327 days.

(21) Appl. No.: 10/806,419

(22) Filed: Mar. 23, 2004

(65) Prior Publication Data

US 2004/0156843 A1   Aug. 12, 2004

Related U.S. Application Data

(63) Continuation-in-part of application No. 09/935,145, filed on Aug. 22, 2001, now abandoned.

(60) Provisional application No. 60/227,152, filed on Aug. 22, 2000.

(51) Int. Cl.
     *C07K 16/00* (2006.01)

(52) U.S. Cl. .................................. 530/387.1

(58) Field of Classification Search ..................... None
     See application file for complete search history.

(56) References Cited

FOREIGN PATENT DOCUMENTS

| WO | WO/9421294 A1 * | 9/1994 |
| WO | WO/9515982 A2 * | 6/1995 |

OTHER PUBLICATIONS

Zetter (Annu. Rev. Med., 1998, v49. pp. 407-424).*
MSNBC News Services, "Mixed results on new cancer drug", Nov. 9, 2000.*
Gura (Science, v278, 1997, pp. 1041-1042).*
Jain (Scientific American Jul. 1994: 58-65).*
Dillman (Annals of Internal Medicine, vol. 111, pp. 592-603, 1989).*
Weiner (Seminars Oncology, vol. 26, No. 4, 1999, pp. 41-50).*
Rudikoff et al (Proc Natl Acad Sci USA 1982 vol. 79 p. 1979-1983).*
Panka et al (Proc Natl Acad Sci USA vol. 85 3080-3084 May 1988).*
Amit et al Science vol. 233 747-753 1986.*

* cited by examiner

*Primary Examiner*—Christopher Yaen

(57) ABSTRACT

The present invention provides a treatment for mammalian diseases characterized by pathological angiogenesis. The treatment consists of administering therapeutically active dosages of peptides containing specific amino acid sequences or antibodies that bind to cell membrane antigens on the surface of rapidly dividing endothelial cells.

8 Claims, 7 Drawing Sheets

Figure 1

Amino Acid Sequence of EP01 (SEQ ID NO:1)

F G <u>K R E Q A E E E R Y F R A Q S R E</u> Q L A A L

The underlined section of the peptide corresponds to motif JJZX$_a$Z$_b$JX$_c$JXJXJXZ Amino Acid Sequence of EP02 (SEQ ID NO:4)

G M D E L S <u>E E D K L T V S R A R K I Q R</u> F

The underlined section of the peptide corresponds to motif ZZZJXXXXJXJJXXJ

Amino Acid Sequence of EP03 (SEQ ID NO:7)

S L Q D I I A I L G M D E L S <u>E E D K L T</u> C

The underlined section of the peptide corresponds to motif ZZZJXXX

Figure 6

DNA Sequence for V_H (SEQ ID NO:8)

GAGGTGAASGTGGTGGAATCTGGGGGAGGCTTAGTGAAGCCTGGAGGGTCCCTGAAACT
CTCCTGTGCAGCCTCTGGATTCACTTTCAGTAGCTATGCCATGTCTTGGGTTCGCCAGA
CTCCAGAGAAGAGGCTGGAGTGGGTCGCATCCATTAGTAGTGGTGGTAGCACCTACTAT
CCAGACAGTGTGAAGGGCCGATTCACCATCTCCAGAGATAATGCCAGGAACATCCTGTA
CCTGCAAATGAGCAGTCTGAGGTCTGAGGACACGGCCATGTATTACTGTGCAAGAGGCC
TACCATTTGCTTACTGGGGCCAAGGGACTCTGGTCACTGTCTCTGCAGAGAGTCAGTCC
TTCCCAAATGTC

Amino Acid Sequence for V_H (SEQ ID NO:20)

```
         10          20          30          40          50
EVXVVESGGG  LVKPGGSLKL  SCAASGFTFS  SYAMSWVRQT  PEKRLEWVAS 60          70          80          90         100
ISSGGSTYYP  DSVKGRFTIS  RDNARNILYL  QMSSLRSEDT  AMYYCARGLP 110         122
FAYWGQGTLV  TVSAESQSFP  NV
```

Figure 7

DNA Sequence for V<sub>L</sub> (SEQ ID NO:9)

GATATTGTGATgACaCAATCTACAGCTTCCTTAGCTGTATCTCTGGGGCAGAGGGCCAC
CATCTCATGCAGGGCCAGCCAAAGTGTCAGTACATCTAGCTATAGTTATATGCACTGGT
ACCAACAGAAACCAGGACAGCCACCCAAACTCCTCATCAAGTATGCATCCAACCTAGAA
TCTGGGGTCCCTGCCAGGTTCAGTGGCAGTGGGTCTGGGACAGACTTCACCCTCAACAT
CCATCCTGTGGAGGAGGAGGATACTGCAACATATTACTGTCAGCACAGTTGGGAGATTC
CGCTCACGTTCGGTGCTGGGACCAAGCTGGAGCTGAAACGGGCTGATGCTGCACCAACT
GTATCC

Amino Acid Sequence for V<sub>L</sub> (SEQ ID NO:21)

```
            10          20          30          40          50
  DIVMTQSTAS  LAVSLGQRAT  ISCRASQSVS  TSSYSYMHWY  QQKPGQPPKL 60          70          80          90         100
  LIKYASNLES  GVPARFSGSG  SGTDFTLNIH  PVEEEDTATY  YCQHSWEIPL 110         120
  TFGAGTKLEL  KRADAAPTVS
```

COMPOSITIONS AND METHODS FOR INHIBITING ANGIOGENESIS

CROSS-REFERENCE TO RELATED APPLICATIONS

The present nonprovisional patent application is a Continuation-In-Part of application Ser. No. 09/935,145 filed Aug. 22, 2001 now abandoned, which in turn claims benefit of provisional patent application entitled "Composition and Methods for Inhibiting Angiogenesis" with filing date Aug. 22, 2000 and patent application number 60/227,152; each of which is herein incorporated by reference.

STATEMENT REGARDING FEDERALLY SPONSORED RESEARCH OR DEVELOPMENT

The United States government may have certain rights in the present invention pursuant to grant number SBIR/1R43CA094698-01 from the National Institutes of Health.

BACKGROUND OF THE INVENTION

Angiogenesis or neovascularization is the formation of new blood vessels from pre-existing capillaries via a mechanism that involves degradation of the basement membrane which surrounds the parent vessel, migration of endothelial cells through the degraded membrane, proliferation of the migrating cells, endothelial cell differentiation, and loop formation (Folkman, J., Angiogenesis and angiogenesis inhibition: an overview, *EXS.,* 79, 1-8 (1997)). With the exception of wound healing and menstruation, angiogenesis in adults is observed only in pathological situations such as cancer, atherosclerosis, and psoriasis, where it contributes to the progression and symptom manifestation of the disease (Folkman, J. Angiogenesis in cancer, vascular, rheumatoid and other disease, *Nat. Med.* 1(1), 27-31 (1995)). Other "angiogenesis-related" diseases include endometriosis, Kaposi's sarcoma and other HIV-related conditions, leukemia, scleroderma, pyogenic granuloma, myocardial angiogenesis, corneal diseases, rubeosis, neovascular glaucoma, diabetic retinopathy, macular degeneration, and retrolental fibroplasia. As used herein, the term "angiogenesis-related diseases" means pathological conditions that require endothelial cell proliferation for progression and symptom manifestation (Chappey, O., et al. Endothelial cells in culture: an experimental model for the study of vascular dysfunctions. *Cell Biol. Toxicol.,* 12(4-6), 199-205 (1996)).

Increasing experimental evidence suggest that angiogenesis plays an essential role in cancer development. It has been observed that solid tumors neither grow beyond 1-2 mm$^3$ nor metastasize unless they become vascularized (Folkman, J. What is the Evidence that Tumors are Angiogenesis Dependent?, *J. Natl. Canc. Inst.,* 82, 4-6 (1990)). Formation of tumor vasculature is necessary in order to deliver nutrients and oxygen at the tumor site, thus, providing a route for tumor metastasis to distant sites. Compositions that inhibit endothelial cell proliferation and/or migration have been shown to inhibit tumor neovascularization, and to prevent tumor growth and metastasis (Eatock, M. M., et al. Tumour vasculature as a target for anticancer therapy. *Cancer Treat Rev.* 26(3), 191-204 (2000)). Several of these inhibitors are currently under evaluation in human clinical trials (Deplanque, G., et al. Anti-angiogenic agents: clinical trial design and therapies in development, *Eur. J. Cancer,* 36, 1713-1724 (2000)).

Antibodies are proteins synthesized by B lymphocytes usually in response to the presence of a foreign substance, called an antigen (Askonas, B. A. Immunoglobulin synthesis and its induction in B-lymphoid cells, *Acta Endocrinol Suppl (Copenh),* 194, 117-132 (1975)). Antibodies are the recognition elements of the humoral immune response, designed to lyse foreign microorganisms and infected cells via activation of the complement system. Antibodies possess specific affinity for the antigens that induced their formation and they readily complex with them to trigger complement activation. Naturally occurring antibodies consist of two heavy and two light chains linked together by disulfide bonds. Each chain comprises domains of unique sequence responsible for antigen binding (variable domains) and domains of constant sequence involved in complement activation and mediation of antibody-dependent cellular toxicity (constant domains). Furthermore, the variable domains of light ($V_L$) and heavy ($V_H$) chains have similar structure with each domain comprising four somewhat conserved regions, called the framework regions (FR), and three hyper-variable regions, called complementarity determining regions (CDR). Studies have shown that CDRs determine antibody specificity (Ohno et al. Antigen-binding specificities of antibodies are primarily determined by seven residues of $V_H$, *Proc Natl Acad Sci USA,* 82(9), 2945-2949 (1985)). In $V_H$ chains, CDRs are located in the proximity of positions 30-35 (CDR1), 50-65 (CDR2), and 95-102 (CDR3) (Kabat et al. *Sequences of Proteins of Immunological Interest,* 5$^{th}$ edit., NIH Publication no 91-3242 US. Department of Health and Human Services (1991) and Honegger et al.). Yet another numbering scheme for immunoglobulin variable domains: an automatic modeling and analysis tool. *J. Mol. Biol.* 309, 657-670 (2001)). In $V_L$ chains, CDRs are located in the proximity of positions 24-34 (CDR1), 50-56 (CDR2), and 89-97 (CDR3).

Antibodies produced in response to the presence of a single antigen have a common specificity but they are heterogeneous in nature, since they are derived from many different antibody-producing cells. Homogeneous or monoclonal antibodies can be produced through hybridoma cells (Galfre, G. and Milstein, C. Preparation of monoclonal antibodies: strategies and procedures, *Methods Enzymol.,* 73(Pt B), 3-46 (1981)). The hybridoma cell method of producing large amounts of homogeneous populations of antibodies with a particular specificity has allowed the use of monoclonal antibodies as diagnostic and therapeutic agents (Milstein, C. With the benefit of hindsight, *Immunol. Today,* 21(8), 359-64 (2000)).

Initially, animal-derived monoclonal antibodies had limited therapeutic value in humans due to antigenicity. The problem was solved with the production of humanized antibodies. Humanized antibodies are defined as immunoglobulin variants or fragments capable of binding to a predetermined antigen and which comprise a FR region having substantially the amino acid sequence of a human immunoglobulin and a CDR region having substantially the amino acid sequence of a non-human immunoglobulin (Hurle, M. R. and Gross, M. Protein engineering techniques for antibody humanization, *Curr. Opin. Biotechnol.,* 5(4), 428-33(1994)). Humanized antibodies have been recently approved for the treatment of various diseases including cancer. Trastuzumab, a humanized antibody against HER-2 receptor, is used for the treatment of breast cancer, while Rituximab, a humanized antibody against CD20, is used for the treatment of lymphoma (Baselga, et al. Phase II study of weekly intravenous trastuzumab (Herceptin) in patients with HER2/neu-overexpressing metastatic breast cancer, *Semin.*

Oncol., 26(4 Suppl 12), 78-83 (1999); Slamon et al. Use of chemotherapy plus a monoclonal antibody against HER2 for metastatic breast cancer that overexpresses HER2, *N. Engl. J. Med.,* 344(11), 783-92 (2001); Byrd et al. Rituximab using a thrice weekly dosing schedule in B-cell chronic lymphocytic leukemia and small lymphocytic lymphoma demonstrates clinical activity and acceptable toxicity, *J. Clin. Oncol.,* 19(8), 2153-64 (2001)).

Humanized antibodies are usually produced recombinantly. Recombinant production of immunoglobulin variants or fragments requires: a. the isolation and sequencing of the DNA encoding the immunoglobulin variants or fragments and b. the insertion of the isolated DNA into a replicable vector for further cloning (amplification) or expression. DNA encoding fragments of interest is often isolated from cDNA by using appropriate oligonucleotide probes capable of binding to specific genes (e.g., those encoding the heavy and light chains of the monoclonal antibodies). cDNA is obtained by reverse transcription of RNA isolated via conventional methods from hybridoma cells producing the monoclonal antibody of interest. Once isolated, DNA may be placed into a variety of expression vectors, which are then transfected into host cells such as *E. coli* or Chinese hamster ovary (CHO) cells for intracellular or extracellular production of the antibody variant or fragment of interest. Intracellular production of an antibody or antibody fragment requires its purification from lysates of host cells, while extracellular production requires purification from supernatants of host cells.

Typically, recombinant antibody constructs consist of modified forms of the antigen-binding portion of an antibody, also known as Fv. Single chain Fv molecules (scFv) usually comprise $V_H$ and $V_L$ domains joined with a small peptide linker in a single polypeptide chain. scFv molecules exhibiting antitumor properties are particularly desired in cancer therapy because their small size (~30 Kd) allows for tumor penetration. Unfortunately, their small size also facilitates increased blood clearance (Hudson et al. Recombinant antibody constructs in cancer therapy, *Curr. Opin. Immunol.,* 11, 548-557 (1999)). To reduce blood clearance and to increase functional affinity (scFv are monovalent), scFv dimers and trimers have been produced. Formation of multimeric scFv complexes usually depends on the length of the linker between $V_H$ and $V_L$ domains. Short linkers (5-10 residues) result in the formation of scFv dimers (also known as diabodies), while linkers with less than three residues in length result in the formation of trimers (also known as triabodies) (Holliger et al. "Diabodies": Small bivalent and bispecific antibody fragments, *Proc. Natl. Acad. Sci. USA,* 90, 6444-6448 (1993) and Atwell et al. ScFv multimers: length of the linker between $V_H$ and $V_L$ domain dictates precisely the transition between diabodies and triabodies, *Protein Eng.,* 12, 597-604 (1999)).

BRIEF SUMMARY OF THE INVENTION

In accordance with the present invention, compositions and methods are provided for inhibiting angiogenesis and for treating angiogenesis-related diseases.

The compositions provided herein comprise naturally occurring or synthetic peptides containing an amino acid sequence of the following motif:

$JJZX_aZ_bJX_cJXJXJXZ$ (SEQ ID NO:22) or
$ZZZJXXXXJXJJXXJ$ (SEQ ID NO: 23)   (1)

where a=2-3, b=2-3, c=3-4, J is a positively charged amino acid, i.e., arginine (R) or lysine (K), Z is a negatively charged amino acid, i.e., aspartic acid (D) or glutamic acid (E), and X is any amino acid.

Examples of naturally occurring or synthetic peptides containing the amino acid sequence of $JJZX_aZ_bJX_c$ JXJXJXZ include the following:

```
FGKREQAEEERYFRAQSREQLAAL      (SEQ ID NO:1)

FGKREQAEEERYFRARAKEQLAAL      (SEQ ID NO:2)

FVKRERATEDFFVRQREKEQLRHL      (SEQ ID NO:3)
```

An example of a naturally occurring or synthetic peptide containing the amino acid sequence of ZZZJXXXXJXJJXXJ includes the following:

G M D E L S E E D K L T V S R A R K I Q R F (SEQ ID NO:4)

In further embodiments, the invention provides compositions comprising antibodies that bind to peptides containing an amino-acid sequence of the previously mentioned motif (1). In a yet another embodiment, the invention provides compositions comprising scFv molecules of an antibody binding to SEQ ID NO: 4.

The methods provided herein for treating angiogenesis-related diseases involve administering to a human or animal a composition containing therapeutic dosages of a naturally occurring protein, protein fragments, or peptides containing an amino acid sequence of the previously mentioned motif (1).

In further embodiments, the invention provides methods for treating angiogenesis-related diseases comprise administering to a human or animal a composition containing therapeutic dosages of an antibody that binds to a peptide containing an amino acid sequence of the previously mentioned motif (1).

Thus, it is an object of the present invention to provide compositions and methods for inhibiting angiogenesis.

It is another object of the present invention to provide methods and compositions for treating cancer by inhibiting tumor neovascularization.

BRIEF DESCRIPTION OF DRAWINGS

FIG. 1 is a schematic diagram showing the sequence of peptides EP01 (SEQ ID NO: 1), EP02 (SEQ ID NO: 4), and EP03 (SEQ ID NO: 7) containing amino acid sequences of the previously mentioned motif (1).

FIG. 6 is a diagram depicting the DNA sequence (A) encoding the $V_H$ domain of B2G4 and the corresponding amino acid sequence (B). Highlighted amino acid sequences indicate potential CDRs.

FIG. 7 is a diagram depicting the DNA sequence (A) encoding the $V_L$ domain of B2G4 and the corresponding amino acid sequence (B). Highlighted amino acid sequences indicate potential CDRs.

COMPOUNDS ACCORDING TO THE INVENTION

Figure 2:
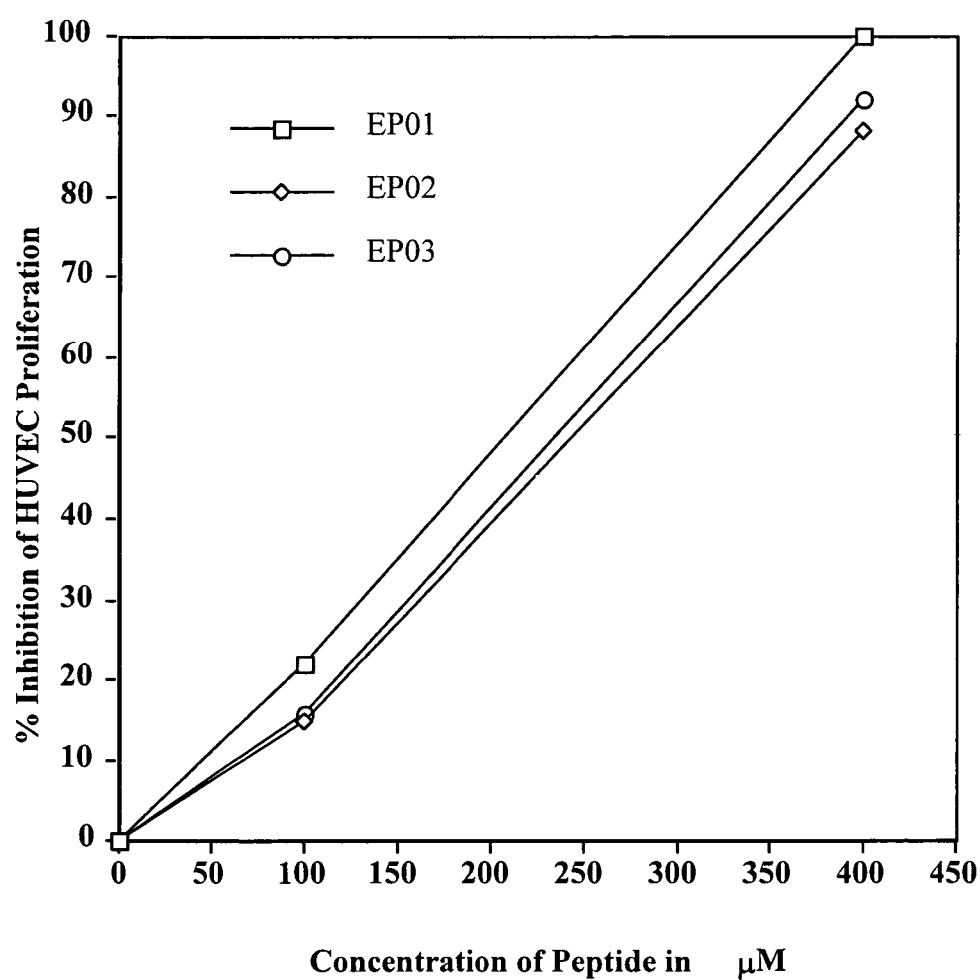
FIG. 2. is a graph depicting the ability of peptides EP01 (SEQ ID NO: 1) (open squares), EP02 (SEQ ID NO: 4) (open diamonds), and EP03 (SEQ ID NO: 7) (open circles) to inhibit basic fibroblast growth factor (bFGF)-induced proliferation of human umbilical vein endothelial cells (HUVECs).

As described below, compounds, which are useful in accordance with the invention, include naturally occurring and synthetic peptides containing an amino acid sequence of the previously mentioned motif (1) and antibodies that bind to naturally occurring and synthetic peptides containing an amino acid sequence of the previously mentioned motif (1). Synthetic peptides include but are not limited to peptides EP01 (SEQ ID NO: 1) and EP02 (SEQ ID NO: 4). Naturally occurring peptides include but are not limited to $F_1$-ATPase inhibitor protein ($F_1$I) (SEQ ID NO: 5) and the beta (β) subunit of $F_1$-ATPase (SEQ ID NO: 6).

DETAILED DESCRIPTION OF THE INVENTION

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The present invention comprised of methods and compositions for treating angiogenesis-related diseases in a human or animal. The treatment comprises the administration of a peptide or antibody in sufficient amount to inhibit endothelial cell proliferation or migration and to suppress angiogenesis-related diseases.

I. Definitions

The terms "a", "an" and "the" as used herein are defined to mean one or more and include the plural unless the context is inappropriate.

The term "peptides" relates to chains of amino acids whose alpha carbons are linked through peptide bonds formed by a condensation reaction between the carboxyl group of the alpha carbon of one amino acid and the amino group of the alpha carbon of another amino acid. A peptide has two terminal amino acids, one amino acid with a free amino-group called the amino- or N-terminus and one amino acid with a free carboxyl group called the carboxyl- or C-terminus. In a peptide, amino acids are numbered starting at the amino terminus and increasing in the direction of the carboxyl-terminus.

Peptides are produced chemically or recombinant. Solid phase is the preferred method for chemical synthesis of peptides. It involves the attachment of the C-terminal amino acid to an insoluble support and the sequential addition of the remaining amino acids. An alternative method for synthesizing amino acids is the recombinant nucleic acid method, which involves the generation of a nucleic acid sequence encoding the peptide, followed by the expression of the peptide in a host and isolation and purification of the expressed peptide.

The term "antibody" refers to monoclonal, polyclonal, multispecific (formed from at least two intact antibodies), or humanized antibodies as well as antibody fragments so long as they possess the desired biological activity. Monoclonal antibodies are obtained through the hybridoma method or the recombinant DNA method, or isolated from phage display antibody libraries. Techniques for antibody production through the previously mentioned methodologies are known to those skilled in the art. Multispecific or chimeric antibodies are prepared using synthetic proteins methods known in the art. Humanization of an antibody can be achieved by substituting non-human CDRs for the corresponding sequences of a human antibody as described by Jones et al., Nature, 321: 522-525 (1986) and Riechmann et al., Nature, 332:323-327 (1988). Antibody fragments can be produced via proteolytic digestion or recombinant methods known in the art.

As used herein, the term "single chain Fv or scFv" molecule refers to a recombinantly produced antibody fragment comprising the $V_H$ and $V_L$ domains of an antibody in a single polypeptide chain. Usually, an scFv molecule also includes a short amino acid sequence between the $V_H$ and $V_L$ domains, which enables the scFv molecule to form the appropriate structure for antigen binding. As used herein, the term "linker" refers to the amino acid sequence that links $V_H$ to $V_L$ in an scFv molecule.

As used herein, the terms "diabody" and "triabody" refer to complexes consisting of two and three scFv molecules, respectively.

As used herein, the term "angiogenesis-related" diseases refers to pathological situations that require formation of new blood vessels for progression and symptom manifestation. Such diseases include, but are not limited to, cancer (solid tumor and leukemias), granulomas, abnormal wound healing, atherosclerosis, rheumatoid arthritis, psoriasis, diabetic retinopathy, macular degeneration, endometriosis, and Kaposi's sarcoma, diabetic neovascularization, peptic ulcer, and scleroderma.

Antibodies and antibody-binding fragments with sequences homologous to those described herein are also included in the present invention. Homologues are those antibodies and antibody-binding fragments with amino acid sequences that have sequence identity or homology with amino acid sequence of the B2G4 antibodies of the present invention. Preferably identity is with the amino acid sequence of the variable regions of the B2G4 antibodies of the present invention. "Sequence identity" and "sequence homology" as applied to an amino acid sequence herein is defined as a sequence with at least about 90%, 91%, 92%, 93%, or 94% sequence identity, and more preferably at least about 95%, 96%, 97%, 98%, or 99% sequence identity to another amino acid sequence, as determined, for example, by the FASTA search method in accordance with Pearson and Lipman, Proc. Natl. Acad. Sci. USA 85, 2444-2448 (1988).

II. Suitable Methods for Practicing the Invention

Inhibition of Endothelial Cell Proliferation

Anti-angiogenic activity is evaluated by testing the ability of a peptide or an antibody to inhibit endothelial cell growth in vitro. An endothelial cell proliferation assay typically involves the routine culturing of the endothelial cells to confluency in the appropriate media. Subsequently, the cells are trypsinized and plated in a 96-well plate at 5,000 cell per well. The cells are cultured for 96 hours in the presence of the peptide or antibody and growth factors. Cell proliferation is then determined using spectrophotometry (MTT assay, BrdU assay) or fluorimetry (Cyquant assay).

Inhibition of Tumor Growth

Ability to inhibit angiogenesis-related diseases is evaluated by testing the ability of a peptide or an antibody to suppress tumor growth in vivo. In a primary tumor growth assay, a certain number of tumor cells such as B16 melanoma cells are injected subcutaneously in C57/J6 mice. The tumor cells are allowed to grow; treatment is initiated when the tumors become palpable. Tumor size is measured every day or every other day. The experiment is terminated at a pre-determined time point.

Administration

The compositions described previously may be administered by the topical, oral, rectal or parenteral (intravenous, subcutaneous or intramuscular) route. They may also be incorporated into biodegradable polymers for sustained release implanted at the disease site. The dosage of the compositions depends on the condition treated, the activity of the drug used, the route of administration, and other clinical factors such as severity of the disease and weight of the patient. The compositions are formulated in ways suitable for the specific route of administration. Formulations suitable for oral administration include capsules, cachets or tablets containing a predetermined amount of the active ingredient, powder or granules, solutions, suspensions, and emulsions. Formulations suitable for topical administration in the mouth include lozenges, pastilles, and mouthwashes. Formulations suitable for topical administration to the skin include ointments, creams, gels, pastes, and transdermal patches. Formulations for rectal administration may be presented as a suppository with a suitable base, while vaginal administrations maybe presented as pessaries, tampons, creams, gels, pastes, foams, and sprays comprising the active ingredient in an appropriate carrier. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

The invention is further understood by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Effect of EP01 (SEQ ID NO: 1), EP02 (SEQ ID NO: 4), and EP03 (SEQ ID NO: 7) Peptides on the bFGF-induced Proliferation of HUVECs.

Proliferation assays familiar to those skilled in the art using human umbilical vein endothelial cells (HUVECs) were employed in order to determine the effect of various peptides and antibodies on the growth of bFGF-stimulated HUVECs.

Materials and Methods

The materials for this experiment included endothelial cells (HUVECs) and media for their proliferation (Media 200, fetal bovine serum (FBS), gelatin, bFGF) (Paragon Bioservices, Baltimore, Md.), and Cell Titer 96 for detection of cell proliferation (Paragon Bioservices, Baltimore, Md.).

Peptides EP01 (SEQ ID NO: 1), EP02 (SEQ ID NO: 4), and EP03 (SEQ ID NO: 7) were synthesized by Multiple Peptide Systems (San Diego, Calif.).

HUVECs were routinely cultured to confluency in Media 200 containing 10% FBS. The cells were then trypsinized and plated in a 96-well plate pre-coated with 1% gelatin at 5000 cells per well per 100 µL Media 200 containing 2% FBS. The cells were allowed to adhere for 24 hours. Subsequently, the media were aspirated and fresh Media 200 containing 0.5% FBS were added to the wells followed by the addition of various concentrations of peptides in the presence and absence of 20 ng/ml bFGF. The assay plates were incubated at 37° C., 5% $CO_2$ for 48 hours. At the end of the incubation period, cell proliferation was determined using cell counting (Cell Counter Model Z1, Coulter Incorporation, Miami, Fla.) or spectrophotometry. In the later case, the assay plates were incubated with Cell Titer 96 for 2 hours and the absorbance was recorded at 490 nm. The effect of the various peptides on the proliferation of endothelial cells was expressed as % inhibition. % Inhibition is defined by the following formula:

$$\frac{[\text{absorbance of cells treated with } bFGF] - [\text{absorbance of cells treated with } bFGF \text{ and peptide}]}{[\text{absorbance of cells treated with } bFGF] - [\text{absorbance of untreated cells}]} \times 100 =$$

% Inhibition of Proliferation

Results

Peptides EP01 (SEQ ID NO: 1), EP02 (SEQ ID NO: 4), and EP03 (SEQ ID NO: 7) tested, here inhibited bFGF-induced HUVEC proliferation. The relative antiproliferative effects of EP01 (SEQ ID NO: 1), EP02 (SEQ ID NO: 4), and EP03 (SEQ ID NO: 7) are shown graphically in FIG. 2. For each point of FIG. 2, the error is less than 10%. % Inhibition is defined in Materials and Methods. The $IC_{50}$ values of the antiproliferative effect of the peptides are reported below:

| Peptide | $IC_{50}$ of Antiproliferative Effect |
|---|---|
| EP01 (SEQ ID NO: 1) | 210 µM |
| EP02 (SEQ ID NO: 4) | 235 µM |
| EP03 (SEQ ID NO: 7) | 245 µM |

EXAMPLE 2

Production of Murine Polyclonal Antisera that Bind EP02 (SEQ ID NO: 4) and EP03 (SEQ ID NO: 7).

Antibody production protocols familiar to those skilled in the art were employed in order to produce murine polyclonal sera, which recognize and bind to peptides with specific amino acid sequences.

Materials and Methods

Peptides EP02 (SEQ ID NO: 4) and EP03 (SEQ ID NO: 7) were conjugated with KLH, a highly immunogenic copper-containing protein, using a commercially available kit (Pierce, product number 77622). The resulting conjugated peptides were used for immunization of mice. After two booster immunizations, the mice were bled and murine anti-EP02 and anti-EP03 antisera were obtained. Various dilutions of these antisera were tested for their ability to bind 96-well plates coated with 2 µg/ml EP02 and EP03. Specifically, 96-well plates were incubated for 2 hrs at room temperature with 50 µl per well of either 2 µg/ml EP02 or 2 µg/ml EP03 in 50 mM Carbonate-Bicarbonate buffer, pH 9.6 (Sigma, St. Louis, Mo.). Subsequently, the wells were emptied and non-specific binding was blocked with 200 µl of 3% non-fat dry milk in PBS (BioWhittaker, Md.) (30 minutes, room temperature). The wells were washed three times with 300 µl PBS containing 0.1% Tween-20. A volume of 50 µl of polyclonal antisera diluted in PBS-0.1% Tween-20 was then added to the wells. After a 60 min incubation at room temperature, the wells were emptied and washed. This was followed by the addition of 50 µl of secondary antibody (goat anti-mouse IgG and IgM peroxidase-labeled abs) diluted in 200 µl PBS containing 0.1% Tween-20. After a 30-min incubation at room temperature, the wells were washed and 50 µl of a peroxidase substrate (ABTS, Kirkegaard and Perry) were added. Binding was measured at 405 nm.

Results

Figure 3A:
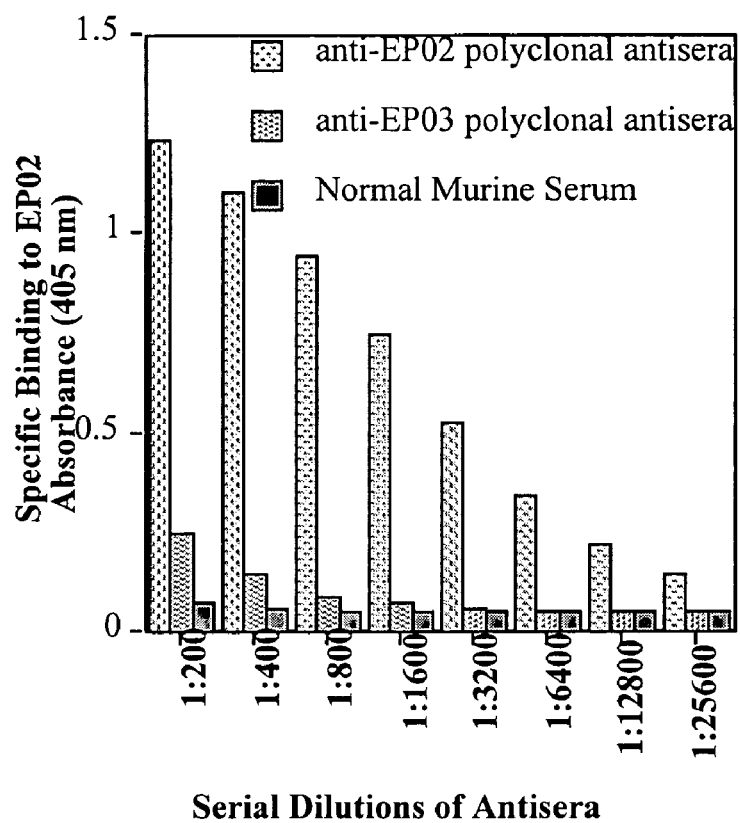
FIG. 3A and FIG. 3B are graphs depicting the ability of murine polyclonal antisera raised against peptides EP02 (SEQ ID NO: 4), designated herein as anti-EP02, and EP03 (SEQ ID NO: 7), designated herein as anti-EP03, and normal murine serum to specifically bind to peptides EP02 (SEQ ID NO: 4) (FIG. 3A) and EP03 (SEQ ID NO: 7) (FIG. 3B).
Figure 3B:
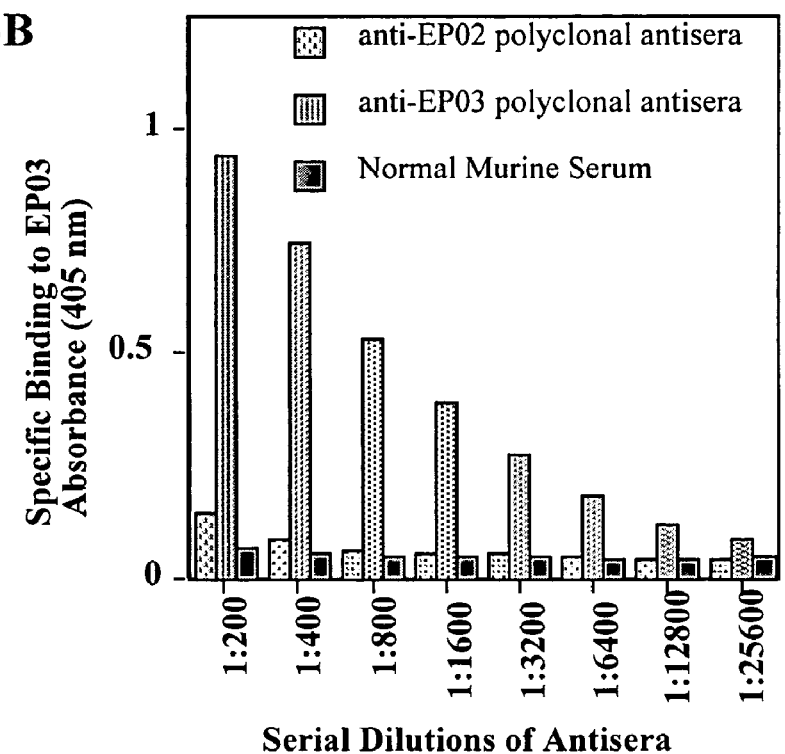

Both peptides were shown to be highly immunogenic as shown in FIG. 3. There was no cross-reactivity between the different antisera.

EXAMPLE 3

Production of Monoclonal Antibodies, Which Recognize and Bind EP02 (SEQ ID NO: 4) and EP03 (SEQ ID NO: 7).

Monoclonal antibody production protocols familiar to those skilled in the art were employed in order to produce monoclonal abs, which recognize and bind to peptides with specific amino acid sequences Materials and Methods.

Monoclonal antibodies (B2G4 and D2G11), which recognize and bind EP02 (SEQ ID NO: 4) and EP03 (SEQ ID NO: 7) respectively, were generated from previously produced antisera according to well-known methods of antibody production (Seon et al. Monoclonal antibody that defines a unique human T-cell leukemia antigen, *Proc. Natl. Acad. USA*, 80, 845-849 (1983)). B2G4 and D2G11 mabs specifically recognized EP02 (SEQ ID NO: 4) and EP03 (SEQ ID NO: 7), respectively. These abs were also able to bind to the cell surface of HUVECs, as measured by a cell-based binding assay. Specifically, HUVECs were plated at 75% confluency in 96-well plates and stimulated with 2 ng/ml bFGF. After overnight incubation, the wells were emptied and washed with cold PBS. This was followed by addition of 200 µl of the binding buffer (10 mM MOPS pH 6.7 containing 250 mM sucrose and 0.4 mM ATP). The cells were then incubated with 20 µg of ab for 2 hrs at 37° C. Subsequently, the wells were emptied and washed. After incubation with a fluorescein-labeled secondary ab for 30 min at 37° C., specific binding is measured with a fluorometer.

Results

Figure 4:
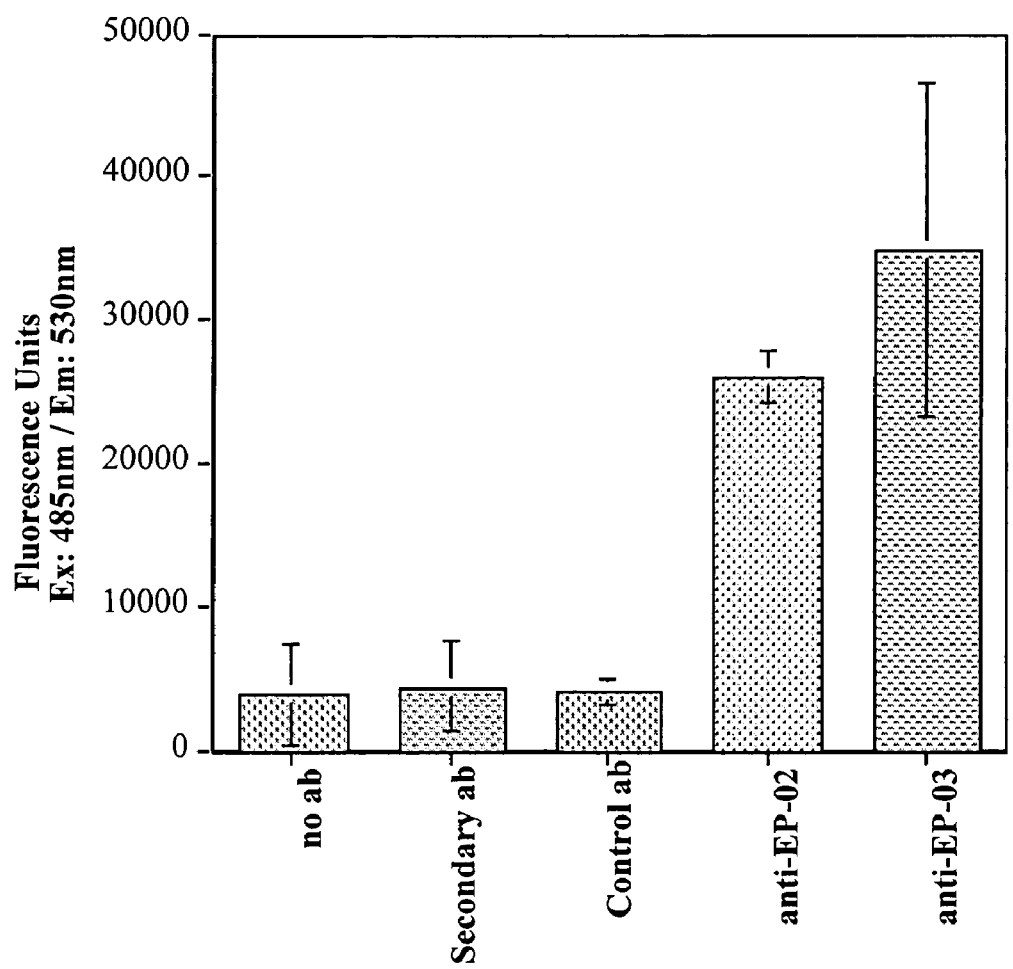
FIG. 4 is a graph depicting the ability of a murine anti-EP02 monoclonal antibody (mab), named B2G4, and a murine anti-EP03 mab, named D2G11, to specifically bind on the cell surface of HUVECs.

Monoclonal abs that recognize and bind EP02 (SEQ ID NO: 4) and EP03 (SEQ ID NO: 7) bind to the cell surface of proliferating HUVECs, as depicted in FIG. 4.

EXAMPLE 4

Monoclonal abs B2G4 and D2G11 Inhibit bFGF-induced Proliferation of HUVECs.

Materials and Methods

HUVEC proliferation assays in the presence of abs were performed as previously described.

Results.

Figure 5:
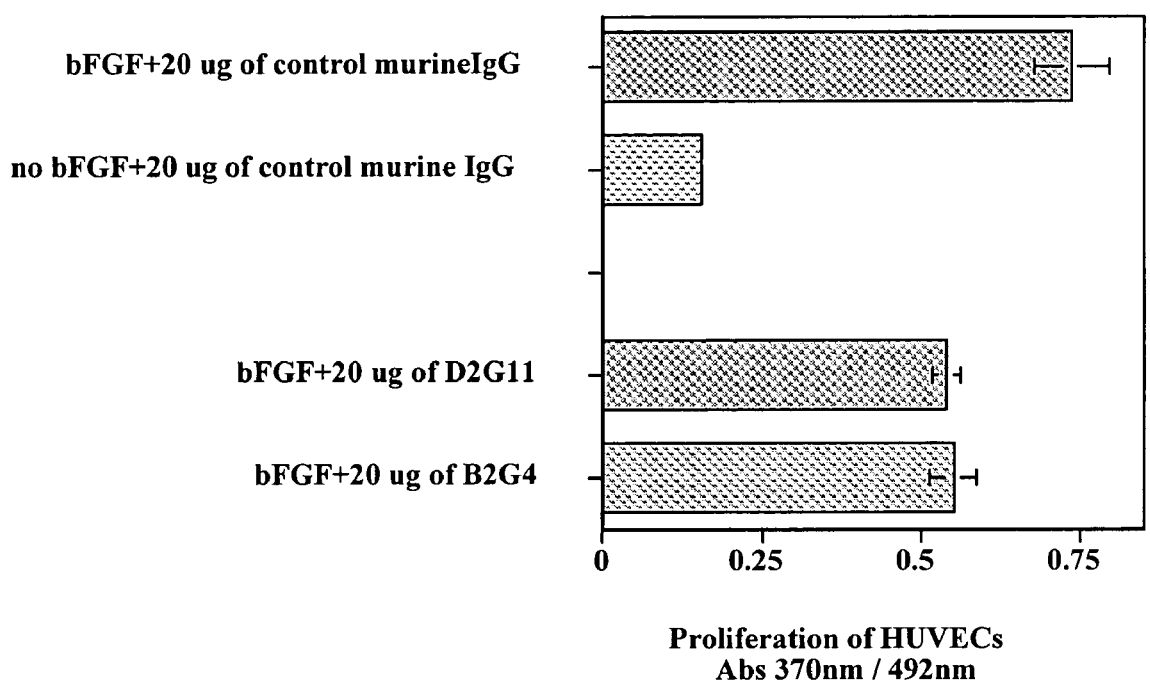
FIG. 5 is a graph depicting the ability of B2G4 and D2G11 to inhibit bFGF-induced proliferation of HUVECs.

B2G4 and D2G11 mabs induce significant inhibition of bFGF-induced proliferation of HUVECs, as depicted in FIG. 5.

EXAMPLE 5

Isolation and Sequencing of DNA Encoding the $V_H$ and $V_L$ Domains of B2G4.

Materials and Methods

Approximately $1 \times 10^7$ hybridoma cells producing B2G4 antibody were grown in T-75 flasks and then harvested for RNA isolation using S.N.A.P.™ Total RNA Isolation Kit from Invitrogen (Carlsbad, Calif.) according to the manufacturer's instructions. cDNA was synthesized using reverse transcriptase (SuperScript™ III One-Step RT-PCR System with Platinum® Taq DNA Polymerase kit from Invitrogen). PCR amplification was performed in a 100 µL reaction volume using 2 µL cDNA, 1 µL 10 mM dNTPs, 10 µL Taq polymerase buffer, 2.5 U Taq polymerase (from Promega, Madison, Wis.), and 20 pmol 5' or 3' primers in $H_2O$. Specific primers used herein were: heavy chain forward, a mixture of 5'-ctt ccg gaattc SAR GTN MAG CTG SAG SAG TC-3' (SEQ ID NO:10), 5'-ctt ccg gaattc SAR GTN MAG CTG SAG SAG TCW GG-3' (SEQ ID NO:11), 5'-cct ccg gaattc CAG GTT ACT CTG AAA GWG TST G-3' (SEQ ID NO:12), 5'-ctt ccg gaattc GAG GTC CAR CTG CAA CAR TC-3' (SEQ ID NO:13), 5'-ctt ccg gaattc CAG GTC CAA CTV CAG CAR CC-3' (SEQ ID NO:14), 5'-ctt ccg gaattc GAG GTG AAS STG GTG GAA TC-3' (SEQ ID NO:15), 5'-ctt ccg gaattc GAT GTG AAC TTG GAA GTG TC-3' (SEQ ID NO:16), heavy chain reverse, 5'-gga agatct GAC ATT TGG GAA GGA CTG ACT CTC-3 (SEQ ID NO: 17), light chain forward, 5'-gg gagctc GAY ATT GTG MTS ACM CAR WCT MCA-3' (SEQ ID NO: 18), and light chain reverse, 5'-ggt gcatgc GGA TAC AGT TGG TGC AGC ATC-3' (SEQ ID NO:19) (Wang et al. Universal PCR amplification of mouse immunoglobulin gene variable regions: the design of degenerate primers and an assessment of the effect of DNA polymerase 3' to 5' exonuclease activity, *J. Immunol Methods*, 233, 167-177 (2000)). The underlined letters in the primer sequences represent cloning sites, EcoRI (gaattc), BglII (agatct), SacI (gagctc), and SphI (gcatgc). For both heavy and light chains, forward primers are degenerates with S=C or G, R=G or A, N=A, C, G or T, M=A or C, W=A or T, V=A, C or G, and Y=C or T. Separate reactions were set up for heavy and light chains. Cycling conditions were: 94° C. for 3 min, 30 cycles of a three-step program (94° C., 1 min; 45° C., 1 min; and 72° C., 2 min), 72° C. for 10 min, and then cooled to 4° C. (Perkin Elmer 9700). Amplified fragments were digested and separated on a 1% TAE gel. DNA was recovered from the agarose slices using a Geneclean II kit (Qbiogene, Carlsbad, Calif.). $V_H$ and $V_L$ fragments were cloned into the pUC19 vector and expressed in DH10B™ *E. coli* cells (Invitrogen). Plasmid DNA was isolated using the SNAP MiniPrep kit and sequenced by Retrogen (San Diego, Calif.).

Results

The results are shown in FIG. 6 and FIG. 7. DNA sequence for $V_H$ and $V_L$ fragments are:

$V_H$ sequence from EcoRI to BglII (SEQ ID NO: 8):

gaattcGAGGTGAASGTGGTGGAATCTGGGGGAGGCTTAGTGAAGCCTGG

AGGGTCCCTGAAACTCTCCTGTGCAGCCTCTGGATTCACTTTCAGTAGCT

ATGCCATGTCTTGGGTTCGCCAGACTCCAGAGAAGAGGCTGGAGTGGGTC

GCATCCATTAGTAGTGGTGGTAGCACCTACTATCCAGACAGTGTGAAGGG

CCGATTCACCATCTCCAGAGATAATGCCAGGAACATCCTGTACCTGCAAA

TGAGCAGTCTGAGGTCTGAGGACACGGCCATGTATTACTGTGCAAGAGGC

```
CTACCATTTGCTTACTGGGGCCAAGGGACTCTGGTCACTGTCTCTGCAGA

GAGTCAGTCCTTCCCAAATGTCagatct
```

V_L sequence from SacI to SphI (SEQ ID NO: 9):

```
gagctcGATATTGTGATgACaCAatCTACAGCTTCCTTAGCTGTATCTCT

GGGGCAGAGGGCCACCATCTCATGCAGGGCCAGCCAAAGTGTCAGTACAT

CTAGCTATAGTTATATGCACTGGTACCAACAGAAACCAGGACAGCCACCC

AAACTCCTCATCAAGTATGCATCCAACCTAGAATCTGGGGTCCCTGCCAG

GTTCAGTGGCAGTGGGTCTGGGACAGACTTCACCCTCAACATCCATCCTG
```

```
TGGAGGAGGAGGATACTGCAACATATTACTGTCAGCACAGTTGGGAGATT ccGCTCaCGTTCGGTGCTGGGACCAAGCTGGAGCTGAAACGGGCTGATGC

TGCACCAACTGTATCCgcatgc
```

Comparison of the amino acid sequences encoded by SEQ ID NO: 8 and SEQ ID NO: 9 with the amino acid sequences of $V_H$ and $V_L$ domains of known murine antibodies (Carter et al. Humanization of an anti-p185HER2 antibody for human cancer therapy, *Proc Natl. Acad. Sci. USA* 89, 4285-4289 (1992)) suggests that the highlighted areas of FIGS. 6 and 7 represent potential CDR domains for the heavy and light chains of B2G4 antibody.

---

I claim:

1. An isolated antibody or antigen-binding fragment, wherein said isolated antibody or antigen-binding fragment comprises a heavy chain comprising the amino acid sequence encoded by nucleotides 1 to 378 of SEQ ID NO: 8, and wherein said isolated antibody or antigen-binding fragment specifically binds the peptide of SEQ ID NO: 4.

2. An isolated antibody or antigen-fragment, wherein said isolated antibody or antigen-binding fragment comprises a light chain comprising the amino acid sequence encoded by nucleotides 1 to 372 of SEQ ID NO: 9, and wherein said isolated antibody or antigen-binding fragment specifically binds the peptide of SEQ ID NO: 4.

3. An isolated antibody or antigen-binding fragment, wherein said isolated antibody or antigen-binding fragment comprises at least one heavy and at least one light chain, and wherein said heavy chain comprises the amino acid sequence encoded by nucleotides 1 to 378 of SEQ ID NO: 8, and wherein said light chain comprises the amino acid sequence encoded by nucleotides 1 to 372 of SEQ ID NO: 9, and wherein said antibody or antigen-binding fragment specifically binds to the peptide of SEQ ID NO: 4.

4. The antibody or antigen-binding fragment according to claim 1, wherein said antigen-binding fragment is a scFV fragment.

5. The antibody or antigen-binding fragment according to claim 2, wherein said antigen-binding fragment is a scFV fragment.

6. The antibody or antigen-binding fragment according to claim 3, wherein said antigen-binding fragment is a scFV fragment.

7. The antibody or antigen-binding fragment according to claim 3, wherein said antigen-binding fragment is a diabody.

8. The antibody or antigen-binding fragment according to claim 3, wherein the antigen-binding fragment is a triabody.

* * * * *

SEQUENCE LISTING

<160> NUMBER OF SEQ ID NOS: 21

<210> SEQ ID NO 1
<211> LENGTH: 24
<212> TYPE: PRT
<213> ORGANISM: Artificial Sequence
<220> FEATURE:
<223> OTHER INFORMATION: Synthetic peptide

<400> SEQUENCE: 1

Phe Gly Lys Arg Glu Gln Ala Glu Glu Glu Arg Tyr Phe Arg Ala Gln
1               5                   10                  15

Ser Arg Glu Gln Leu Ala Ala Leu
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide

<400> SEQUENCE: 2

Phe Gly Lys Arg Glu Gln Ala Glu Glu Glu Arg Tyr Phe Arg Ala Arg
1               5                   10                  15

Ala Lys Glu Gln Leu Ala Ala Leu
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic peptide

<400> SEQUENCE: 3

Phe Val Lys Arg Glu Arg Ala Thr Glu Asp Phe Phe Val Arg Gln Arg
1               5                   10                  15

Glu Lys Glu Gln Leu Arg His Leu
            20

```
<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Gly Met Asp Glu Leu Ser Glu Asp Lys Leu Thr Val Ser Arg Ala
1               5                   10                  15

Arg Lys Ile Gln Arg Phe
            20

<210> SEQ ID NO 5
<211> LENGTH: 81
<212> TYPE: PRT
<213> ORGANISM: Homo sapiens

<400> SEQUENCE: 5

Gly Ser Asp Gln Ser Glu Asn Val Asp Arg Gly Ala Gly Ser Ile Arg
1               5                   10                  15

Glu Ala Gly Gly Ala Phe Gly Lys Arg Glu Gln Ala Glu Glu Glu Arg
            20                  25                  30

Tyr Phe Arg Ala Gln Ser Arg Glu Gln Leu Ala Ala Leu Lys Lys His
        35                  40                  45

His Glu Glu Glu Ile Val His His Lys Lys Glu Ile Glu Arg Leu Gln
    50                  55                  60

Lys Glu Ile Glu Arg His Lys Leu Lys Ile Lys Met Leu Lys His Asp
65                  70                  75                  80

Asp

<210> SEQ ID NO 6
<211> LENGTH: 539
<212> TYPE: PRT
<213> ORGANISM: Homo sapiens

<400> SEQUENCE: 6

Met Thr Ser Leu Trp Gly Lys Gly Thr Gly Cys Lys Leu Phe Lys Phe
1               5                   10                  15

Arg Val Ala Ala Ala Pro Ala Ser Gly Ala Leu Arg Arg Leu Thr Pro
            20                  25                  30

Ser Ala Ser Leu Pro Pro Ala Gln Leu Leu Arg Ala Val Arg Arg
        35                  40                  45

Arg Ser His Pro Val Arg Asp Tyr Ala Ala Gln Thr Ser Pro Ser Pro
    50                  55                  60

Lys Ala Gly Ala Ala Thr Gly Arg Ile Val Ala Val Ile Gly Ala Val
65                  70                  75                  80

Val Asp Val Gln Phe Asp Glu Gly Leu Pro Pro Ile Leu Asn Ala Leu
            85                  90                  95

Glu Val Gln Gly Arg Glu Thr Arg Leu Val Leu Glu Val Ala Gln His
            100                 105                 110

Leu Gly Glu Ser Thr Val Arg Thr Ile Ala Met Asp Gly Thr Glu Gly
        115                 120                 125

Leu Val Arg Gly Gln Lys Val Leu Asp Ser Gly Ala Pro Ile Lys Ile
    130                 135                 140

Pro Val Gly Pro Glu Thr Leu Gly Arg Ile Met Asn Val Ile Gly Glu
145                 150                 155                 160
```

-continued

```
Pro Ile Asp Glu Arg Gly Pro Ile Lys Thr Lys Gln Phe Ala Pro Ile
            165                 170                 175

His Ala Glu Ala Pro Glu Phe Met Glu Met Ser Val Glu Gln Glu Ile
            180                 185                 190

Leu Val Thr Gly Ile Lys Val Val Asp Leu Leu Ala Pro Tyr Ala Lys
            195                 200                 205

Gly Gly Lys Ile Gly Leu Phe Gly Gly Ala Gly Val Gly Lys Thr Val
210                 215                 220

Leu Ile Met Glu Leu Ile Asn Asn Val Ala Lys Ala His Gly Gly Tyr
225                 230                 235                 240

Ser Val Phe Ala Gly Val Gly Glu Arg Thr Arg Glu Gly Asn Asp Leu
            245                 250                 255

Tyr His Glu Met Ile Glu Ser Gly Val Ile Asn Leu Lys Asp Ala Thr
            260                 265                 270

Ser Lys Val Ala Leu Val Tyr Gly Gln Met Asn Gln Pro Pro Gly Ala
            275                 280                 285

Arg Ala Arg Val Ala Leu Thr Gly Leu Thr Val Ala Glu Tyr Phe Arg
            290                 295                 300

Asp Gln Glu Gly Gln Asp Val Leu Leu Phe Ile Asp Asn Ile Phe Arg
305                 310                 315                 320

Phe Thr Gln Ala Gly Ser Glu Val Ser Ala Leu Leu Gly Arg Ile Pro
            325                 330                 335

Ser Ala Val Gly Tyr Gln Pro Thr Leu Ala Thr Asp Met Gly Thr Met
            340                 345                 350

Gln Glu Arg Ile Thr Thr Thr Lys Gly Ser Ile Thr Ser Val Gln
            355                 360                 365

Ala Ile Tyr Val Pro Ala Asp Asp Leu Thr Asp Pro Ala Pro Ala Thr
            370                 375                 380

Thr Phe Ala His Leu Asp Ala Thr Thr Val Leu Ser Arg Ala Ile Ala
385                 390                 395                 400

Glu Leu Gly Ile Tyr Pro Ala Val Asp Pro Leu Asp Ser Thr Ser Arg
            405                 410                 415

Ile Met Asp Pro Asn Ile Val Gly Ser Glu His Tyr Asp Val Ala Arg
            420                 425                 430

Gly Val Gln Lys Ile Leu Gln Asp Tyr Lys Ser Leu Gln Asp Ile Ile
            435                 440                 445

Ala Ile Leu Gly Met Asp Glu Leu Ser Glu Glu Asp Lys Leu Thr Val
450                 455                 460

Ser Arg Ala Arg Lys Ile Gln Arg Phe Leu Ser Gln Pro Phe Gln Val
465                 470                 475                 480

Ala Glu Val Phe Thr Gly His Met Gly Lys Leu Val Pro Leu Lys Glu
            485                 490                 495

Thr Ile Lys Gly Phe Gln Gln Ile Leu Ala Gly Glu Tyr Asp His Leu
            500                 505                 510

Pro Glu Gln Ala Phe Tyr Met Val Gly Pro Ile Glu Glu Ala Val Ala
            515                 520                 525

Lys Ala Asp Lys Leu Ala Glu Glu His Ser Ser
530                 535
```

```
<210> SEQ ID NO 7
<211> LENGTH: 22
<212> TYPE: PRT
<213> ORGANISM: Artificial Sequence
<220> FEATURE:
<223> OTHER INFORMATION: Synthetic peptide
```

<400> SEQUENCE: 7

Ser Leu Gln Asp Ile Ile Ala Ile Leu Gly Met Asp Glu Leu Ser Glu
1               5                   10                  15

Glu Asp Lys Leu Thr Cys
            20

<210> SEQ ID NO 8
<211> LENGTH: 378
<212> TYPE: DNA
<213> ORGANISM: Mus musculus

<400> SEQUENCE: 8
gaattcgagg tgaasgtggt ggaatctggg ggaggcttag tgaagcctgg agggtccctg      60
aaactctcct gtgcagcctc tggattcact ttcagtagct atgccatgtc ttgggttcgc     120
cagactccag agaagaggct ggagtgggtc gcatccatta gtagtggtgg tagcacctac     180
tatccagaca gtgtgaaggg ccgattcacc atctccagag ataatgccag gaacatcctg     240
tacctgcaaa tgagcagtct gaggtctgag gacacggcca tgtattactg tgcaagaggc     300
ctaccatttg cttactgggg ccaagggact ctggtcactg tctctgcaga gagtcagtcc     360
ttcccaaatg tcagatct                                                   378

<210> SEQ ID NO 9
<211> LENGTH: 372
<212> TYPE: DNA
<213> ORGANISM: Mus musculus

<400> SEQUENCE: 9
gagctcgata ttgtgatgac acaatctaca gcttccttag ctgtatctct ggggcagagg      60
gccaccatct catgcagggc cagccaaagt gtcagtacat ctagctatag ttatatgcac     120
tggtaccaac agaaaccagg acagccaccc aaactcctca tcaagtatgc atccaaccta     180
gaatctgggg tccctgccag gttcagtggc agtgggtctg gacagactt caccctcaac      240 atccatcctg tggaggagga ggatactgca acatattact gtcagcacag ttgggagatt     300
ccgctcacgt tcggtgctgg gaccaagctg gagctgaaac gggctgatgc tgcaccaact     360
gtatccgcat gc                                                          372

<210> SEQ ID NO 10
<211> LENGTH: 32
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t

<400> SEQUENCE: 10
cttccggaat tcsargtnma gctgsagsag tc                                    32

<210> SEQ ID NO 11
<211> LENGTH: 35
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t

```
<400> SEQUENCE: 11
cttccggaat tcsargtnma gctgsagsag tcwgg                           35

<210> SEQ ID NO 12
<211> LENGTH: 34
<212> TYPE: DNA
<213> ORGANISM: Artificial Sequence
<220> FEATURE:
<223> OTHER INFORMATION: PCR primer

<400> SEQUENCE: 12
cctccggaat tccaggttac tctgaaagwg tstg                            34

<210> SEQ ID NO 13
<211> LENGTH: 32
<212> TYPE: DNA
<213> ORGANISM: Artificial Sequence
<220> FEATURE:
<223> OTHER INFORMATION: PCR primer

<400> SEQUENCE: 13
cttccggaat tcgaggtcca rctgcaacar tc                              32

<210> SEQ ID NO 14
<211> LENGTH: 32
<212> TYPE: DNA
<213> ORGANISM: Artificial Sequence
<220> FEATURE:
<223> OTHER INFORMATION: PCR primer

<400> SEQUENCE: 14
cttccggaat tccaggtcca actvcagcar cc                              32

<210> SEQ ID NO 15
<211> LENGTH: 32
<212> TYPE: DNA
<213> ORGANISM: Artificial Sequence
<220> FEATURE:
<223> OTHER INFORMATION: PCR primer

<400> SEQUENCE: 15
cttccggaat tcgaggtgaa sstggtggaa tc                              32

<210> SEQ ID NO 16
<211> LENGTH: 32
<212> TYPE: DNA
<213> ORGANISM: Artificial Sequence
<220> FEATURE:
<223> OTHER INFORMATION: PCR primer

<400> SEQUENCE: 16
cttccggaat tcgatgtgaa cttggaagtg tc                              32

<210> SEQ ID NO 17
<211> LENGTH: 33
<212> TYPE: DNA
<213> ORGANISM: Artificial Sequence
<220> FEATURE:
<223> OTHER INFORMATION: PCR primer

<400> SEQUENCE: 17
ggaagatctg acatttggga aggactgact ctc                             33
```

<210> SEQ ID NO 18
<211> LENGTH: 32
<212> TYPE: DNA
<213> ORGANISM: Artificial Sequence
<220> FEATURE:
<223> OTHER INFORMATION: PCR primer

<400> SEQUENCE: 18
gggagctcga yattgtgmts acmcarwctm ca					32

<210> SEQ ID NO 19
<211> LENGTH: 30
<212> TYPE: DNA
<213> ORGANISM: Artificial Sequence
<220> FEATURE:
<223> OTHER INFORMATION: PCR primer

<400> SEQUENCE: 19
ggtgcatgcg gatacagttg gtgcagcatc					30

<210> SEQ ID NO 20
<211> LENGTH: 122
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Glu Val Xaa Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Leu Pro Phe Ala Tyr Trp Gly Gln Gly Thr Leu Val Thr Val
            100                 105                 110

Ser Ala Glu Ser Gln Ser Phe Pro Asn Val
        115                 120

<210> SEQ ID NO 21
<211> LENGTH: 120
<212> TYPE: PRT
<213> ORGANISM: Mus musculus

<400> SEQUENCE: 21

Asp Ile Val Met Thr Gln Ser Thr Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

```
Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
            85                  90                  95

Glu Ile Pro Leu Thr Phe Gly Ala Gly Thr Lys Leu Glu Leu Lys Arg
            100                 105                 110

Ala Asp Ala Ala Pro Thr Val Ser
        115                 120
```